United States Patent
Hofer et al.

(10) Patent No.: US 6,500,416 B2
(45) Date of Patent: Dec. 31, 2002

(54) PESTICIDE

(75) Inventors: Dieter Hofer, Liestal (CH); Max Angst, Magden (CH); Pierre-Joseph Charmillot, Trélex (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/790,943

(22) Filed: Feb. 22, 2001

(65) Prior Publication Data

US 2001/0021378 A1 Sep. 13, 2001

Related U.S. Application Data

(63) Continuation of application No. 09/180,397, filed as application No. PCT/EP97/02246 on May 2, 1997, now abandoned.

(30) Foreign Application Priority Data

May 9, 1996 (CH) ............................................. 1180/96

(51) Int. Cl.$^7$ .................. A01N 25/00; A01N 31/00; A01N 35/00; A01N 37/00
(52) U.S. Cl. .................. 424/84; 424/405; 514/595; 514/599; 514/613; 514/675; 514/677; 514/681; 514/712; 514/715; 514/716; 514/717; 514/718; 514/721; 514/972
(58) Field of Search .................. 424/405, 84; 514/972, 514/183, 241, 277, 279, 299, 300, 315, 317, 326, 359, 403, 449, 461, 476, 478, 480, 482, 483, 506, 507, 510, 579, 580, 585, 715, 716, 717, 718, 740, 741, 742, 595, 599, 613, 675, 677, 681, 712, 721

(56) References Cited

U.S. PATENT DOCUMENTS

| | | | |
|---|---|---|---|
| 4,436,719 A | 3/1984 | Lindaberry | 424/407 |
| 4,666,747 A | 5/1987 | Quinn | 427/421 |
| 4,732,762 A | 3/1988 | Sjogren | 424/409 |
| 4,775,534 A | 10/1988 | Bartlett et al. | 424/410 |
| 4,954,497 A | 9/1990 | Kamikado et al. | 514/235.5 |
| 5,114,977 A * | 5/1992 | Karrer et al. | 514/720 |
| 5,346,920 A * | 9/1994 | Sakamoto | 514/539 |
| 5,612,047 A * | 3/1997 | Duffy et al. | 424/405 |
| 5,707,638 A | 1/1998 | Lösel et al. | 424/407 |
| 5,759,561 A | 6/1998 | Angst et al. | 424/407 |

FOREIGN PATENT DOCUMENTS

| | | | |
|---|---|---|---|
| DE | 3 422 921 | | 1/1985 |
| EP | 055475 | | 7/1982 |
| EP | 229191 | | 7/1987 |
| EP | 376888 | * | 7/1990 |
| GB | 1 548 920 | | 7/1979 |
| GB | 2 063 068 | | 6/1981 |
| GB | 2 064 323 | | 6/1981 |
| GB | 2 141 932 | | 1/1985 |

OTHER PUBLICATIONS

The Pesticide Manual, 10th Edition, pp. 143, 281, 294–295, 363,375, 408, 442–443, 681–682, 730, 868–869, 887–888, 943–944, 1102 (1995).*

Noyaku–Dezain to Kaihatsusuihi, Pesticide Design (Strategy and Tactics), Edited by I. Yamamoto et al. d.(Mar. 31, 1979), K.K. Soft Science, pp. 1039–1050 (Abstract enclosed).

D P LE, Brighton Crop Protection Conference, 1996, 5A–6, pp. 481–486.

Chemical Abstract 101:67821r of Jp 59 59,734, Apr. 5, 1984.

The Pesticide Manual, 10$^{th}$ Edition, pp. 200, 244, 301, 467, 502, 595, 609, 652 and S1081 (1995).

Bradley et al., "Reduction of Egg Hatch in Pear Psylla (Homoptera: Psyllidae) after Contact with Adults with Insect Growth Regulators," J. Econ. Entom. (1995), vol. 88, No. 5, pp. 1420–1424.

* cited by examiner

*Primary Examiner*—Michael G. Hartley
*Assistant Examiner*—Frank Choi
(74) *Attorney, Agent, or Firm*—William A. Teoli, Jr.; Rose M. Allen

(57) ABSTRACT

There are described a flowable composition for controlling harmful insects and representatives of the order Acarina, comprising at least one pesticidally active compound, one or more signal substances selected from the group consisting of pheromones, kairomones and attractants, a UV absorber or a UV absorber mixture and, if appropriate, one or more additives selected from the group consisting of viscosity-regulating thickeners, fillers, solvents and other formulation auxiliaries, which composition comprises 40 to 98% by weight of the UV absorber or the UV absorber mixture, 0.01 to 30% by weight of one or more signal substance(s) and 0.1 to 20% by weight of one or more pesticidally active compound(s) of the formulae (I) to (V) as specified, and a method of controlling harmful insects and representatives of the order Acarina using this composition.

4 Claims, No Drawings

PESTICIDE

This application is a continuation of application Ser. No. 09/180,397, filed on Nov. 9, 1998, now abandoned, which a 371 of PCT/EP97/02246, filed on May 2, 1997 now abandoned.

The present invention relates to a novel pesticidal composition for controlling harmful insects and representatives of the order Acarina, and to a method of controlling these pests with the composition in question.

When controlling plant pests, in particular insects and spider mites in agricultural crops, especially in monocultures, it is an aim to keep the contact between not only the crop plants, but also their environment and the soil in which they grow, and the pesticidally active ingredients to a minimum. However, it is nevertheless intended to expose the pests themselves, which are mainly found on the plants, to the active ingredient as intensely as possible, for example by contact action or by action as a stomach poison. It is furthermore attempted to ensure that the adverse effects of the pesticidally active ingredients on beneficial animals and warm-blooded species are not substantial. To achieve these aims, pesticides and control methods have been proposed whose principal is that the behaviour of the target pests can be controlled or altered, with the aid of signal substances, for example using pheromones, in such a way that the pests are led to a source of a pesticidal active ingredient, which source is provided in separate areas within the cultivated area to be protected (so-called attract-and-kill methods, EP-A-376 888). Such methods have been successful in particular for controlling adult pests. However, the control of larvae of these pests, using these methods, is very poor indeed since these larvae are generally of low mobility and will therefore hardly find the source of the signal substances and thus the pesticide. Naturally, in contrast, eggs of those pests cannot be controlled at all using such methods. Thus, if one intends to achieve that, on the one hand, not only the crop plants to be protected, but also the soil in which they grow, come into as little contact as possible with pesticidally active ingredients but, on the other hand, the pests found on the plants are exposed to the active ingredients as intensely as possible while simultaneously leaving the beneficial animals unharmed, the method of choice will be the attract-and-kill methods described in the literature. However, as discussed, one will have to accept that it is hardly possible, using this method, to control the larvae present in the crop, and not at all possible to control the eggs which have been deposited in the period during which the crop has been treated with the composition in question. Thus, this means that the crop may be reinfested with the pest a short time after the treatment. There is therefore still a demand for a method of controlling pests which, in the manner described above, not only leaves plants and environment largely unharmed, but which is also capable of destroying not only the adults, but in particular the eggs and larvae, very especially preferably the eggs, of the pests so as to prevent the pest from spreading further.

The abovementioned shortcomings are overcome by control method and composition according to the invention. The invention relates to a flowable composition for controlling harmful insects and representatives of the order Acarina, comprising at least one pesticidally active compound, one or more signal substances selected from the group consisting of pheromones, kairomones and attractants, a UV absorber or a UV absorber mixture and, if appropriate, one or more additives selected from the group consisting of viscosity-regulating thickeners, fillers, solvents and other formulation auxiliaries, which comprises 40 to 98% by weight of the UV absorber or of the UV absorber mixture, 0.01 to 30% by weight of one or more signal substance(s), and 0.1 to 20% by weight of one or more pesticidally active compound(s) selected from the group consisting of the compounds of the formula

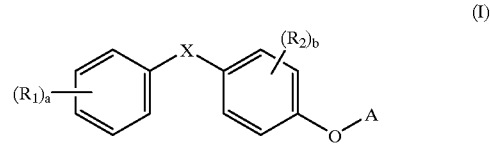

(I)

in which a is 0, 1 or 2 especially 0, where, if a is 2, the two radicals $R_1$ are identical or different, b is 0, 1 or 2, especially 0, where, if b is 2, the two radicals $R_2$ are identical or different;

X is methylene, O, S or C(=O), especially O, $R_1$ is $C_1$–$C_3$alkyl, halo-$C_1$–$C_3$alkyl, $C_1$–$C_3$alkoxy, halo-$C_1$–$C_3$alkoxy, fluorine, chlorine or bromine, especially fluorine or chlorine;

$R_2$ is halogen, nitro, $C_1$–$C_6$alkyl, phenyl-$C_1$–$C_6$alkyl, halo-$C_1$–$C_4$alkyl, $C_1$–$C_3$alkoxy, halo-$C_1$–$C_3$alkoxy, $C_2$–$C_4$alkenyl, $C_2$–$C_4$alkynyl, $C_1$–$C_3$alkoxyalkyl or $C_3$–$C_6$cycloalkyl, and A is $C_1$–$C_6$alkyl, $C_2$–$C_6$alkenyl or $C_3$–$C_6$alkynyl, which are unsubstituted or substituted by a substituent selected from the group consisting of $C_1$–$C_6$alkoxy, $C_2$–$C_6$alkenyloxy, $C_3$–$C_6$alkynyloxy, —O—N=CH$_2$, —O—N=CH—$C_1$–$C_6$alkyl, phenoxy, pyridyl, pyridyloxy, phenyl and phenyl, which is substituted by a substituent selected from the group consisting of $C_1$–$C_6$alkyl or —O—CH$_2$—O—, especially pyridyloxy, $C_2$–$C_6$alkenyl or $C_3$–$C_6$alkynyl which are unsubstituted or substituted by a substituent selected from the group consisting of halogen, $C_1$–$C_6$alkoxy, $C_1$–$C_6$alkylcarbonyl, $C_1$–$C_6$alkoxycarbonyl and $C_1$–$C_6$aminocarbonyl;

A is a radical

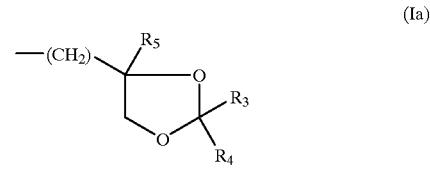

(Ia)

where either $R_3$ is $C_1$–$C_6$alkyl, halo-$C_1$–$C_3$alkyl, $C_2$–$C_4$alkenyl, $C_2$–$C_4$alkynyl, $C_1$–$C_3$alkoxy or $C_3$–$C_6$cycloalkyl, especially $C_1$–$C_4$alkyl, and $R_4$ is hydrogen or $C_1$–$C_3$alkyl, especially hydrogen, or $R_3$ and $R_4$, together with the carbon atom to which $R_3$ and $R_4$ are bonded, are a ring having 4, 5 or 6 ring members, where the ring skeleton, which may contain a carbon-carbon double bond, is either constructed from carbon atoms only or may contain one oxygen atom and where the ring is unsubstituted or mono- or disubstituted by identical or different $C_1$–$C_3$alkyl; and $R_5$ is hydrogen or $C_1$–$C_3$alkyl, especially H; or
a radical

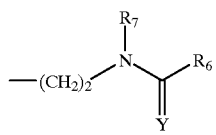
(Ib)

where $R_6$ is $C_1$–$C_6$alkyl, phenyl-$C_1$–$C_6$alkyl, halo-$C_1$–$C_4$alkyl, $C_2$–$C_4$alkenyl, $C_2$–$C_4$alkynyl, $C_1$–$C_6$alkoxy, phenoxy, phenyl-$C_1$–$C_6$alkoxy, halo-$C_1$–$C_4$alkoxy or $C_3$–$C_6$cycloalkyl, especially $C_1$–$C_6$alkyl or $C_1$–$C_4$alkoxy, in particular $C_1$–$C_4$alkoxy;

$R_7$ is hydrogen, $C_1$–$C_6$alkyl, phenyl-$C_1$–$C_6$alkyl, halo-$C_1$–$C_4$alkyl, $C_2$–$C_4$alkenyl, $C_2$–$C_4$alkynyl, $C_1$–$C_3$alkoxyalkyl or $C_3$–$C_6$cycloalkyl, especially H; and
Y is O or S, especially O;
in free form or in salt form;
isopropyl (E,E)-(R,S)-11-methoxy-3,7,11-trimethyl-dodeca-2,4-dienoate (methoprene); or
prop-2-ynyl (±) (E,E)-3,7,11-trimethyl-dodeca-2,4-dienoate (kinoprene);
of the formula

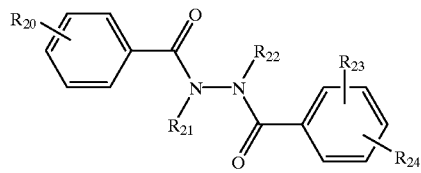
(II)

in which $R_{20}$, $R_{23}$ and $R_{24}$ independently of one another are hydrogen, halogen, $C_1$–$C_8$alkyl, $C_3$–$C_6$cycloalkyl, halo-$C_3$–$C_6$cycloalkyl, halo-$C_1$–$C_8$alkyl, $C_1$–$C_8$alkoxy, $C_1$–$C_4$alkoxy-$C_1$–$C_4$alkyl or halo-$C_1$–$C_8$-alkoxy, especially $C_1$–$C_2$alkyl; and $R_{21}$, and $R_{22}$ independently of one another are H, $C_1$–$C_8$alkyl, $C_3$–$C_6$cycloalkyl, halo-$C_3$–$C_6$cycloalkyl or halo-$C_1$–$C_8$-alkyl, especially H or $C_1$–$C_4$alkyl;
in free form or in salt form;
of the formula

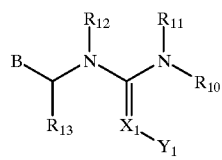
(III)

in which
$R_{10}$ is hydrogen or $C_1$–$C_4$alkyl;
$R_{11}$, is hydrogen, $C_1$–$C_6$alkyl or $C_3$–$C_6$cycloalkyl
$R_{12}$ is H, $C_1$–$C_6$alkyl or $C_3$–$C_7$cycloalkyl, or
$R_{11}$ and $R_{12}$ together are —$CH_2$—$CH_2$—, —$CH_2$—$CH_2$—$CH_2$—, —$CH_2$—O—$CH_2$—, —$CH_2$—S—$CH_2$—, —$CH_2$—NH—$CH_2$—, —$CH_2$—N($CH_3$)—$CH_2$— or —$CH_2$—N($C_2H_5$)—$CH_2$—;
$R_{13}$ is H or $C_1$–$C_4$alkyl, especially H;
$X_1$ is N or C-E;
E is H or —CH(OH)-halo-$C_1$–$C_6$alkyl, especially H;
$Y_1$ is CN or $NO_2$, especially $NO_2$; and B is an unsubstituted or substituted aromatic or non-aromatic monocyclic or bicyclic heterocyclic radical which can contain, depending on the substitution possibility on the ring system, independently of one another one to three substituents selected from the group consisting of $C_1$–$C_3$alkyl, $C_1$–$C_3$alkoxy, halogen, $C_1$–$C_3$haloalkyl having 1 to 7 halogen atoms, cyclopropyl, halocyclopropyl having 1 to 3 halogen atoms, $C_2$–$C_3$alkenyl, $C_2$–$C_3$alkynyl, $C_2$–$C_3$haloalkenyl and $C_2$–$C_3$haloalkynyl having 1 to 4 halogen atoms, $C_1$–$C_3$haloalkoxy having 1 to 7 halogen atoms, $C_1$–$C_3$alkylthio, $C_1$–$C_3$haloalkylthio having 1 to 7 halogen atoms, allyloxy, propargyloxy, allylthio, propargylthio, haloallyloxy, haloallylthio and cyano, especially halogen, very particularly chlorine; in free form or in salt form, if appropriate tautomers, in free form or in salt form;
of the formula

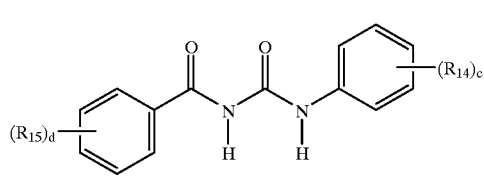
(IV)

in which
c is 0 to 5, especially 3, where, if c is greater than 1, the radicals $R_{14}$ are independent of one another, and
d is 0 to 5, especially 2, where, if d is greater than 1, the radicals $R_{15}$ are independent of one another,
$R_{14}$ is halogen, $C_1$–$C_8$alkyl, $C_3$–$C_6$cycloalkyl, halo-$C_1$–$C_6$alkyl, $C_1$–$C_8$alkoxy, $C_3$–$C_6$cycloalkoxy, halo-$C_1$–$C_8$alkoxy, aryloxy or heteroaryloxy, substituted aryloxy or heteroaryloxy or a group —$CH_2$—O—N=C($R_{16}$)$R_{17}$, especially fluorine, chlorine and halo-$C_1$–$C_3$alkoxy;
$R_{15}$ is halogen, $C_1$–$C_8$alkyl, $C_3$–$C_6$cycloalkyl, halo-$C_3$–$C_6$cycloalkyl, halo-$C_1$–$C_8$alkyl, $C_1$–$C_8$alkoxy, $C_1$–$C_4$alkoxy-$C_1$–$C_4$alkyl or halo-$C_1$–$C_8$alkoxy, especially fluorine;
with the proviso that, if $(R_{14})_c$ is 4-chloro, 2-fluoro-4-[2-chloro-4-(trifluoromethyl)phenoxy] or 3,5-dichloro-4-[2-chloro-4-(trifluoromethyl)phenoxy], $(R_{15})_d$ is not 2,6-difluoro;
$R_{16}$ and $R_{17}$ independently of one another are $C_1$–$C_4$alkyl, $C_3$–$C_6$cycloalkyl or aryl, which are unsubstituted or substituted; in free form or in salt form;
of the formula

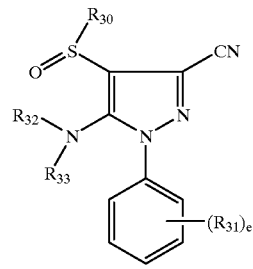
(V)

in which
e is 0, 1, 2 or 3, and $R_{31}$ are identical or different if e is greater than 1,
$R_{30}$ is $C_1$–$C_8$alkyl, phenyl-$C_1$–$C_8$alkyl, $C_3$–$C_6$cycloalkyl, halo-$C_1$–$C_8$alkyl, aryl, heteroaryl or substituted aryl or heteroaryl, especially trifluoromethyl;

$R_{31}$ is halogen, hydroxyl, cyano, nitro, $C_1$–$C_8$alkyl, $C_3$–$C_6$cycloalkyl, halo-$C_3$–$C_6$cycloalkyl, halo-$C_1$–$C_8$alkyl, $C_1$–$C_8$alkoxy, $C_1$–$C_4$alkoxy-$C_1$–$C_4$alkyl or halo-$C_1$–$C_8$alkoxy or $C_1$–$C_8$alkylthio, especially chlorine or trifluoromethyl;

$R_{32}$ and $R_{33}$ independently of one another are hydrogen, $C_1$–$C_8$alkyl, phenyl-$C_1$–$C_8$alkyl, $C_3$–$C_6$cycloalkyl, halo-$C_1$–$C_8$alkyl, aryl, heteroaryl or substituted aryl or heteroaryl, or $R_{32}$ and $R_{33}$ together are a group

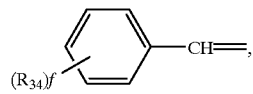

f is 0, 1, 2 or 3, and $R_{34}$ are identical or different if f is greater than 1;

$R_{34}$ is halogen, hydroxyl, cyano, nitro, $C_1$–$C_8$alkyl, $C_3$–$C_6$cycloalkyl, halo-$C_3$–$C_6$cycloalkyl, halo-$C_1$–$C_8$alkyl, $C_1$–$C_8$alkoxy, $C_1$–$C_4$alkoxy-$C_1$–$C_4$alkyl or halo-$C_1$–$C_8$alkoxy or $C_1$–$C_8$alkylthio, especially hydroxyl; in free form or in salt form;

(E)-$N^1$-[(6-chloro-3-pyridyl)methyl]-$N^2$-cyano-$N^1$-methylacetamidine (acetamiprid), in free form or in salt form;

1-tert-butyl-3-(2,6-diisopropyl-4-phenoxyphenyl)thiourea (diafenthiuron), in free form or in salt form; and 2,3,4,5-tetrahydro-3-oxo-4-[(pyridin-3-yl)methyleneamino]-6-methyl-1,2,4-triazine (pymetrozine), in free form or in salt form.

The pesticidally active compounds of the formulae (I) to (V) are preferred in their free form.

Unless otherwise defined, the general terms used hereinabove and hereinbelow have the meanings given hereinbelow.

Halogen—per se or as structural element of groups and compounds such as haloalkyl, haloalkenyl, haloalkoxy and haloalkylthio—is fluorine, chlorine, bromine or iodine, in particular fluorine, chlorine or bromine, mainly fluorine on the one hand and chlorine on the other hand.

Carbon-containing groups and compounds contain, unless otherwise defined, in each case 1 up to and including 9, preferably 1 up to and including 6, preferably 1 up to and including 4, in particular 1 or 2, carbon atoms.

Alkyl—as a group per se and as structural element of other groups and compounds such as haloalkyl, alkoxy, haloalkoxy, alkylthio, haloalkylthio, dialkylaminocarbonyl, alkylcarbonyl and alkoxycarbonyl—is, in each case with due consideration of the specific number of carbon atoms in the group or compound in question, is either straight-chain, i.e. methyl, ethyl, propyl, butyl, pentyl, hexyl, heptyl, octyl or nonyl, or branched, for example isopropyl, isobutyl, sec-butyl, tert-butyl, isopentyl, neopentyl or isooctyl.

In phenylalkyl, an alkyl group bonded to the remaining moiety of the compound I is substituted by a phenyl group, the alkyl group preferably being straight-chain and the phenyl group preferably being bonded in a position higher than the α-position, in particular in the ω-position, of the alkyl group; examples are benzyl, 2-phenyl ethyl and 4-phenylbutyl.

Alkoxyhydroxyalkyl is an alkyl group which is substituted not only by one or more alkoxy groups, but also by one or more hydroxyl groups. Preferred is an alkyl group which is substituted by one alkoxy and one hydroxyl group.

Alkenyl, haloalkenyl, alkenyloxy, alkynyl, haloalkynyl and alkynyloxy are straight-chain or branched and contain in each case two or, preferably, one unsaturated carbon-carbon bond(s). The double or triple bonds of these substituents are preferably separated from the remaining moiety of the compound of the formula I by at least one saturated carbon atom. Examples which may be mentioned are allyl, methallyl, but-2-en-1-yl, but-3-en-2-yl, propargyl, but-2-yn-1-yl and but-3-yn-1-yloxy.

Halogen-substituted carbon-containing groups and compounds, such as haloalkyl, haloalkenyl, haloalkoxy and haloalkylthio, can be partially halogenated or perhalogenated, in the case of polyhalogenation it being possible for the halogen substituents to be identical or different. Examples of haloalkyl—as a group per se and as structural element of other groups and compounds such as haloalkoxy and haloalkylthio,—are methyl which is mono- to trisubstituted by fluorine, chlorine and/or bromine, such as $CHF_2$, $CF_2Cl$, $CFCl_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CF_2Br$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$, $CF_2CF_2CF_3$ or $CH(CF_3)_2$; and butyl or one of its isomers, mono- to nonasubstituted by fluorine, chlorine and/or bromine, such as $CF(CF_3)CHFCF_3$, $CF_2(CF_2)_2CF_3$ or $CH_2(CF_2)_2CF_3$. Haloalkyl $R_1$ is preferably exclusively fluorinated, in particular perfluorinated. Examples of haloalkenyl are 2-chloroprop-2-en-1-yl, 2,3-dichloroprop-2-en-1-yl and 2,3-dibromoprop-2-en-1-yl.

Cycloalkyl is cyclopropyl, cyclobutyl, cyclopentyl or cyclohexyl, preferred is cyclopropyl.

Suitable hetero atoms in the ring skeleton of the heterocyclic radical are all elements of the Periodic Table which can form at least two covalent bonds.

Aryl is phenyl or naphthyl, especially phenyl. Heteroaryl is a five- or 6-membered heterocyclic aromatic radical which contains one or two hetero atoms selected from the group consisting of N, O and S. Preferred radicals b in the compounds of the formula (III) are those which contain one N atom, one N and one S atom or one O atom, especially pyridyl, thiazolyl and tetrahydrofuranyl.

Preferred active substances in the compositions according to the invention are the compounds of the formula (I); especially preferably a composition which comprises a compound of the formula (I) in which a and b are O; or X is O; or A is $C_1$–$C_6$alkyl which is substituted by $C_1$–$C_6$alkoxy, —O—N=$CH_2$, —O—N=CH—$C_1$–$C_6$alkyl, phenoxy, pyridyl, pyridyloxy, or is $C_2$–$C_6$alkenyl or $C_3$–$C_6$alkynyl; or in which A is a radical of the formula (Ia), and $R_3$ is $C_1$–$C_6$alkyl and $R_4$ is hydrogen or $C_1$–$C_3$alkyl and $R_5$ is hydrogen; or in which A is a radical of the formula (Ib), and $R_6$ is $C_1$–$C_6$alkyl or $C_1$–$C_6$alkoxy, $R_7$ is hydrogen and Y is O.

Equally preferred as active substances in the compositions according to the invention are the compounds of the formula (II).

Preferred pesticidally active individual compounds which may be mentioned are:

4-(2-ethyl-1,3-dioxolan-4-ylmethoxy)phenyl phenyl ether, very especially a mixture of 50 to 80% of (2RS,4SR) 4-(2-ethyl-1,3-dioxolan-4-ylmethoxy)phenyl phenyl ether and 50 to 20% of (2RS,4RS) 4-(2-ethyl-1,3-dioxolan-4-ylmethoxy)phenyl phenyl ether (diofenolan);

3-(2-ethyl-1,3-dioxolan-4-ylmethoxy)phenyl fluorophenyl ether;
ethyl 2-(4-phenoxyphenoxy)ethylcarbamate (fenoxycarb);
4-phenoxyphenyl (R,S)-2-(pyridyloxy)propyl ether (pyriproxyfen);
N-tert-butyl-N'-(4-ethylbenzoyl)-3,5-dimethylbenzohydrazide (tebufenozide);
N-tert-butyl-N'-benzoylbenzohydrazide (RH 5849);
RH 2485, of the formula,

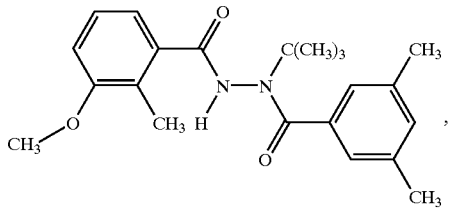

(methoxyfenozide);
ANS 1182;
isopropyl (E,E)-(R,S)-11-methoxy-3,7,11-trimethyldodeca-2,4-dienoate (methoprene);
prop-2-ynyl (±) (E,E)-3,7,11-trimethyidodeca-2,4-dienoate (kinoprene);
(E)-$N^1$-[(6-chloro-3-pyridyl)methyl]-$N^2$-cyano-$N^1$-methylacetamidine (NI-25, acetamiprid);
(±)-5-amino-1-(2,6-dichloro-ααα-trifluoro-p-tolyl)-4-trifluoromethylsulfinylpyrazole-3-carbonitrile (fipronil);
(R,S)-1-[2,5-dichloro-4-(1,1,2,3,3,3-hexafluoropropoxy)phenyl]-3-(2,6-difluorobenzoyl)-urea (lufenuron);
5-[(4-hydroxyphenyl)methyleneamino]-1-(2,6-dichloro-ααα-trifluoro-p-tolyl)-4-trifluoromethylsulfinylpyrazole-3-carbonitrile (vaniliprole);
(6-chloro-3-pyridylmethyl)-N-nitroimidazolidin-2-ylideneamine (imidacloprid);
(E)-N-(2-chlorothiazol-5-ylmethyl)-N-ethyl-N'-methyl-2-nitrovinylidenediamine;
(E)-N-(2-chlorothiazol-5-ylmethyl)-N-methyl-N'-methyl-2-nitrovinylidenediamine;
(E)-N-(6-chloro-3-pyridylmethyl)-N-ethyl-N'-cyclopropyl-2-nitrovinylidenediamine;
(E)-N-(6-chloro-3-pyridylmethyl)-N-ethyl-N'-ethyl-2-nitrovinylidenediamine;
(E)-N-(6-chloro-3-pyridylmethyl)-N-ethyl-N'-methyl-2-nitrovinylidenediamine (nitenpyram);
(E)-N-(6-chloro-3-pyridylmethyl)-N-methyl-N'-methyl-2-nitrovinylidenediamine;
(E)-N-(6-chloro-3-pyridylmethyl)-N-cyclopropyl-N'-methyl-2-nitrovinylidenediamine;
(2-chloropyrid-5-ylmethyl)-3-methyl-4-nitroiminoperhydro-1,3,5-oxadiazine;
(2,3-dichloropyrid-5-ylmethyl)-3-methyl-4-nitroiminoperhydro-1,3,5-oxadiazine;
(2-chloropyrid-5-ylmethyl)-3-ethyl-4-nitroiminoperhydro-1,3,5-oxadiazine;
(2-chloropyrid-5-ylmethyl)-3-cyclopropylyl-4-nitroiminoperhydro-1,3,5-oxadiazine;
(2-chorothiazol-5-ylmethyl)-3-methyl-4-nitrolminoperhydro-1,3,5-oxadiazine;
(2-chlorothiazol-5-ylmethyl)-3-ethyl-4-nitroiminoperhydro-1,3,5-oxadiazine;
(2-chlorothiazol-5-ylmethyl)-3-cyclopropyl-4-nitroiminoperhydro-1,3,5-oxadiazine;
3-methyl-4-nitroimino-5-(1-oxido-3-pyridiniomethyl)perhydro-1,3,5-oxadiazine;
(2-chloro-1-oxido-5-pyridiniomethyl)-3-methyl-4-nitroiminoperhydro-1,3,5-oxadiazine; and
3-methyl-5-(2-methylpyrid-5-ylmethyl)-4-nitroiminoperhydro-1,3,5-oxadiazine.

Especially preferred as pesticidally active compounds for the purposes of the present invention are tebufenozide, diofenolan, fenoxycarb, methoprene, kinoprene and pyriproxyfen. Fenoxycarb is very especially preferred.

The compounds of the formulae (I) to (V) are known to those skilled in the art. In particular, acetamiprid is known from The Pesticide Manual, $10^{th}$Ed. (1994), The British Crop Protection Council, London, page 730;
diafenthiuron from The Pesticide Manual, $10^{th}$Ed. (1994), The British Crop Protection Council, London, page 294;
diofenolan from The Pesticide Manual, $10^{th}$Ed. (1994), The British Crop Protection Council, London, page 363;
3-(2-ethyl-1,3-dioxolan-4-ylmethoxy)phenyl fluorophenyl ether;
fenoxycarb from The Pesticide Manual, $9^{th}$Ed. (1991), The British Crop Protection Council, London, page 375;
fipronil from The Pesticide Manual, $10^{th}$Ed. (1994), The British Crop Protection Council, London, page 463;
imidacloprid from The Pesticide Manual, $9^{th}$Ed. (1991), The British Crop Protection Council, London, page 491;
kinoprene from The Pesticide Manual, $10^{th}$Ed. (1994), The British Crop Protection Council, London, page 1102;
lufenuron from The Pesticide Manual, $10^{th}$Ed. (1994), The British Crop Protection Council, London, page 628;
methoprene from The Pesticide Manual, $10^{th}$Ed. (1994), The British Crop Protection Council, London, page 680;
nitenpyram from The Pesticide Manual, $10^{th}$Ed. (1994), The British Crop Protection Council, London, page 736;
pymetrozine from The Pesticide Manual, $10^{th}$Ed. (1994), The British Crop Protection Council, London, page 868;
pyriproxyfen from The Pesticide Manual, $10^{th}$Ed. (1994), The British Crop Protection Council, London, page 887;
RH 5849 from Brighton Crop Protection Conference, 1996, p. 481-486; and
tebufenozide from The Pesticide Manual, $10^{th}$Ed. (1994), The British Crop Protection Council, London, page 943.

Surprisingly, it has now been found that the present compositions are outstandingly suitable for controlling pests, preferably for controlling eggs and larvae, in particular for controlling the eggs of the above pests, while having a good long-term action, being well tolerated by plants and leaving beneficial animals to a high degree unharmed. Application of the abovementioned signal substances or attractants allows considerably lesser amounts of insecticides, which are frequently toxic to warm-blooded species and beneficial animals, to be used when treating the cultivated areas to be protected. This novel procedure, which is advantageous from the ecological point of view, belongs to the principles of integrated crop protection. This is especially important since, normally, especially high amounts of pesticides must be used for controlling the eggs of pests. In particular, the finding is extremely surprising since the male insects are first attracted by the composition according to the invention which comprises the signal substance(s) and the pesticidally active compound(s), thus taking up the pesticide, and then transfer this pesticide to the female pests, from which it comes into contact with the eggs. It is as yet unknown whether the egg which has been deposited is already contaminated with the active ingredient or whether it comes into contact with the pesticide only after deposition, by means of contact with the female. Apart from this, the process is entirely novel; the possibility of controlling pests, especially their eggs, via this route has as yet not been recognized and opens up novel routes of pest control. The method of controlling pests via this route is therefore termed "attract-and-sterilize" method, in contrast to the "attract-and-kill" method disclosed in, for example, EP-A-376,888. In the method according to the invention, the males are not destroyed, which is in contrast to the "attract-and-kill" method. Nor must the effect be mistaken for the known systemic control of ectoparasites, in particular fleas, in domestic animals and productive livestock. In this last-mentioned method, the pesticidally active compound is administered to the host organism—for example—together with the feed, the pesticide reaches the bloodstream of the host organism and is taken up from the female fleas directly from the blood.

A further important advantage of the application of the compositions according to the invention is the fact that they are active independently of whether the pest population to be controlled consists mainly of females or mainly of males, or whether they are approximately equal in number. This is not the case in the abovementioned "attract-and-kill" method. If, when applying the last-mentioned method, the majority of animals in the population are females, it will be relatively highly probable that the males, which are in the minority, will find one of these females instead of a drop of the pesticidally active agent, and the result will be egg deposition by females which have not taken up pesticide via the males, which means that reproduction takes place. At first, this is also the case in the "attract-and-sterilize" method. However, since the females which have mated no longer give off pheromone and the males which have come into contact with the pheromone are not destroyed, the number of males in the population will in any case exceed the number of females after a very short time, so that the vast majority of females which mate from this point in time on will come into contact with the pesticidally active substance.

The compositions according to the invention are employed for controlling plants-injurious insects in crops of useful plants, afforestations and stands of ornamentals, in cotton, in fruit production and viticulture, in arable crops and in forestry, preferably in fruit production. The compositions are distinguished by a pronounced activity, in particular against larvae and eggs, mainly against eggs.

Furthermore, the compositions according to the invention can also be used for controlling ectoparasitic insects, for example *Lucilia sericata*, and representatives of the order Acarina, mainly ticks such as *Boophilus microplus*, which are injurious to productive livestock and domestic animals, for example by treating the animal houses and the grazing land.

Successful control within the scope of the subject of the invention is possible, in particular, of pests from the orders Lepidoptera, Coleoptera, Orthoptera, Isoptera, Psocoptera, Anoplura, Mallophaga, Thysanoptera, Heteroptera, Homoptera, Hymenoptera, Diptera, Siphonaptera, Thysanura and Acarina, mainly Lepidoptera and Coleoptera. Very especially good control is possible of the following pests:

Abagrotis spp., Abraxas spp., Acantholeucania spp., Acanthoplusia spp., Acarus spp., *Acarus siro*, Aceria spp., *Aceria sheldoni*, Acleris spp., Acoloithus spp., Acompsia spp., Acossus spp., Acria spp., Acrobasis spp., Acrocercops spp., Acrolepia spp., Acrolepiopsis spp., Acronicta spp., Acropolitis spp., Actebia spp., Aculus spp., *Aculus schlechtendali*, Adoxophyes spp., *Adoxophyes reticulana*, Aedes spp., Aegeria spp., Aethes spp., Agapeta spp., Agonopterix spp., Agriopis spp., Agriotes spp., Agriphila spp., Agrochola spp., Agroperina spp., Alabama ssp., *Alabama argillaceae*, Agrotis spp., Albuna spp., Alcathoe spp., Alcis spp., Aleimma spp., Aletia spp., Aleurothrixus spp., *Aleurothrixus floccosus*, Aleyrodes spp., *Aleyrodes brassicae*, Allophyes spp., Alsophila spp., Amata spp., Amathes spp., Amblyomma spp., Amblyptilia spp., Ammoconia spp., Amorbia spp., Amphion spp., Amphipoea spp., Amphipyra spp., Amyelois spp., Anacamptodes spp., Anagrapha spp., Anarsia spp., Anatrychyntis spp., Anavitrinelia spp., Ancylis spp., Andropolia spp., Anhimella spp., Antheraea spp., Antherigona spp., *Antherigona soccata*, Anthonomus ssp., *Anthonomus grandis*, Anticarsia spp., *Anticarsia gemmatalis*, Aonidiella spp., Apamea spp., Aphania spp., Aphelia spp., Aphididae, Aphis spp., Apotomis spp., Aproaerema spp., Archippus spp., Archips spp., Acromyrrnex, Arctia spp., Argas spp., Argolamprotes spp., Argyresthia spp., Argyrogramma spp., Argyroploce spp., Argyrotaenia spp., Arotrophora spp., Ascotis spp., Aspidiotus spp., Aspilapteryx spp., Asthenoptycha spp., Aterpia spp., Athetis spp., Atomaria spp., *Atomaria linearis*, Atta spp., Atypha spp., Autographa spp., Axylia spp., Bactra spp., Barbara spp., Batrachedra spp., Battaristis spp., Bembecia spp., Bemisia spp., *Bemisia tabaci*, Bibio spp., *Bibio hortulanis*, Bisigna spp., Blastesthia spp., Blatta spp., Blatella spp., Blepharosis spp., Bleptina spp., Boarmia spp., Bombyx spp., Bomolocha spp., Boophilus spp., Brachmia spp., Bradina spp., Brevipalpus spp., Brithys spp., Bryobia spp., *Bryobia praetiosa*, Bryotropha spp., Bupalus spp., Busseola spp., *Busseola fusca*, Cabera spp., Cacoecimorpha spp., Cadra spp., *Cadra cautella*, Caenurgina spp., Calipitrimerus spp., Callierges spp., Callophpora spp., *Callophpora erythrocephala*, Calophasia spp., Caloptilia spp., Calybites spp., Capnoptycha spp., Capua spp., Caradrina spp., Caripeta spp., Camienta spp., Carposina spp., *Carposina nipponensis*, Catamacta spp., Catelaphris spp., Catoptria spp., Caustoloma spp., Celaena spp., Celypha spp., Cenopis spp., Cephus spp., Ceramica spp., Cerapteryx spp., Ceratitis spp, Ceratophyllus spp., Ceroplaster spp., Chaetocnema spp., *Chaetocnema tibialis*, Chamaesphecia spp., Charanvca spp., Cheimophila spp., Chersotis spp., Chiasmia spp., Chilo spp., Chionodes spp., Chorioptes spp., Choristoneura spp., Chrysaspidia spp., Chrysodeixis spp., Chrysomya spp., Chrysomphalus spp., *Chrysomphalus dictyospermi*, *Chrysomphalus aonidium*, Chrysoteuchia spp., Cilix spp., Cimex spp., Clysia spp., *Clysia ambiguella*, Clepsis spp., Cnaemidophorus spp., Cnaphalocrocis spp., Cnephasia spp., Coccus spp., *Coccus hesperidum*, Cochylis spp., Coleophora spp., Colotois spp., Commophila spp., Conistra spp., Conopomorpha spp., Corcyra spp., Comutiplusia spp., Cosmia spp., Cosmopolites spp., Cosmopterix spp., Cossus spp., Costaeonvexa spp., Crambus spp., Creatonotos spp., Crocidolomia spp., *Crocidolomia binotalis*, Croesia spp., Crymodes spp., Cryptaspasma spp., Cryptoblabes spp., Cryptocala spp., Cryptophlebia spp., *Cryptophlebia leucotreta*, Cryptoptila spp., Ctenopseustis spp., Cucullia spp., Curculio spp., Culex spp., Cuterebra spp., Cydia spp., *Cydia pomoneila*, Cymbalophora spp., Dactylethra spp., Dacus spp., Dadica spp., Damalinea spp., Dasychira spp., Decadarchis spp., Decodes spp., Deilephila spp., Deltodes spp., Dendrolimus spp., Depressaria spp., Dermestes spp., Dermanyssus spp., *Dermanyssus gallinae*, Diabrotica spp., Diachrysia spp., Diaphania spp., Diarsia spp., Diasemia spp., Diatraea spp., Diceratura spp., Dichomeris spp., Dichrocrocis spp., Dichrorampha spp., Dicycla spp., Dioryctria spp., Diparopsis spp., *Diparopsis castanea*, Dipleurina spp., Diprion spp., Diprionidae, Discestra spp., Distantiella spp., *Distantiella theobroma*, Ditula spp., Diumea spp., Doratopteryx spp., Drepana spp., Drosphila spp., *Drosphila melanogaster*, Dysauxes spp., Dysdercus spp., Dysstroma spp., Eana spp., Eafias spp., Ecclitica spp., Ecdytolopha spp., Ecpyrrhorrhoe spp., Ectomyelois spp., Eetropis spp., Egira spp., Elasmopalpus spp., Emmelia spp., mpoasca spp., Empyreuma spp., Enargia spp., Enarmonia spp., Endopiza spp., Endothenia spp., Endotricha spp., Eoreuma spp., Eotetranychus spp., *Eotetranychus carpini*, Epagoge spp., Epelis spp., Ephestia spp., Ephestiodes spp., Epiblema spp., Epiehofistodes spp., Epinotia spp., Epiphyas spp., Epiplema spp., Epipsestis spp., Epirrhoe spp., Episimus spp., Epitymbia spp., Epilachna spp., Erannis spp., Erastria spp., Eremnus spp., Ereunetis spp., Eriophyes spp., Eriosoma spp., *Eriosoma lanigerum*, Erythroneura spp., Estigmene spp., Ethmia spp., Etiella spp., Euagrotis spp., Eucosma spp., Euehlaena spp., Euelidia spp., Eueosma spp., Euchistus spp., Eucosmomorpha spp., Eudonia spp., Eufidonia spp., Euhyponomeutoides spp., Eulepitodes spp., Eulia spp., Eulithis spp., Eupithecia spp., Euplexia spp., Eupoecilia spp., *Eupoecilia ambiguella*, Euproctis spp., Eupsilia spp., Eurhodope spp., Eurois spp., Eurygaster spp., Eurythmia spp., Eustrotia spp., Euxoa spp., Euzophera spp., Evergestis spp., Evippe spp., Exartema spp., Fannia spp., Faronta spp., Feltia spp., Filatima spp., Fishia spp., Frankliniella spp., Fumibotys spp., Gaesa spp., Gasgardia spp., Gastrophilus spp., Gelechia spp., Gilpinia spp., *Gilpinia polytoma*, Glossina spp., Glyphipterix spp., Glyphodes spp., Gnorimoschemini spp., Gonodonta spp., Gortyna spp., Gracillaria spp., Graphania spp., Grapholita spp., Grapholitha spp., Gravitarmata spp., Gretchena spp., Griselda spp., Gryllotalpa spp., Gynaephora spp., Gypsonoma spp., Hada spp., Haematopinus spp., Halisidota spp., Harpipteryx spp., Harrisina spp., Hedya spp., Helicoverpa spp., Heliophobus spp., Heliothis spp., Hellula spp., Helotropa spp., Hemaris spp., Hercinothrips spp., Herculia spp., Hermonassa spp., Heterogenea spp., Holomelina spp., Homadaula spp., Homoeosoma spp., Homoglaea spp., Homohadena spp., Homona spp., Homonopsis spp., Hoplocampa spp., Hoplodrina spp., Hoshinoa spp., Hxalomma spp., Hydraecia spp., Hydriomena spp., Hyles spp., Hyloicus spp., Hypagyrtis spp., Hypatima spp., Hyphantria spp., *Hyphantria cunea*, Hypocala spp., Hypocoena spp., Hypodema spp., Hyppobosca spp., Hypsipyla spp., Hyssia spp., Hysterosia spp., Idaea spp., Idia spp., Ipimorpha spp., Isia spp., Isochorista spp., Isophrictis spp., Isopolia spp., Isotrias spp., Ixodes spp., Itame spp., Jodia spp., Jodis spp., Kawabea spp., Keiferia spp., *Keiferia lycopersicella*, Labdia spp., Lacinipolia spp., Lambdina spp., Lamprothritpa spp., Laodelphax spp., Lasius spp., Laspeyresia spp., Leptinotarsa spp., *Leptinotarsa decemlineata*, Leptocorsa spp., Leptostales spp., Lecanium spp., *Lecanium comi*, Lepidosaphes spp., Lepisma spp., *Lepisma saccharina*, Lesmone spp., Leucania spp., Leucinodes spp., Leucophaea spp., *Leucophaea maderae*, Leucoptera spp., *Leucoptera scitella*, Linognathus spp., Liposcelis spp., Ussorhoptuis spp., Lithacodia spp., Lithocolletis spp., Lithomoia spp., Uthophane spp., Lixodessa spp., Lobesia spp., *Lobesia botrana*, Lobophora spp., Locusta spp., Lomanaltes spp., Lomographa spp., Loxagrotis spp., Loxostege spp., Lucilia spp., Lymantria spp., Lymnaecia spp., Lyonetia spp., Lyriomyza spp., Macdonnoughia spp., Macrauzata spp., Macronoctua spp., Macrosiphus spp., Malacosoma spp., Maliarpha spp., Mamestra spp., *Mamestra brassicae*, Manduca spp., *Manduca sexta*, Marasmia spp., Margaritia spp., Matratinea spp., Matsumuraeses spp., Melanagromyza spp., Melipotes spp., Melissopus spp., Melittia spp., Melolontha spp., Meristis spp., Meritastis spp., Merophyas spp., Mesapamea spp., Mesogona spp., Mesoleuca spp., Metanema spp., Metendothenia spp., Metzneria spp., Micardia spp., Microcorses spp., Microleon spp., Mnesictena.spp., Mocis spp., Monima spp., Monochroa spp., Monomorium spp., *Monomorium pharaonis*, Monopsis spp., Morrisonia spp., Musca spp., Mutuuraia spp., Myelois spp., Mythimna spp., Myzus spp., Naranga spp., Nedra spp., Nemapogon spp., Neodiprion spp., Neosphaleroptera spp., Nephelodes spp., Nephotettix spp., Nezara spp., Nilaparvata spp., Niphonympha spp., Nippoptilia spp., Noctua spp., Nola spp., Notocelia spp., Notodonta spp., Nudaurelia spp., Ochropleura spp., Ocnerostoma spp., Oestrus spp., Olethreutes spp., Oligia spp., Olindia spp., Olygonychus spp., *Olygonychus gallinae*, Oncocnemis spp., Operophtera spp., Ophisma spp., Opogona spp., Oraesia spp., Omiodoros spp., Orgyia spp., Oria spp., Orseolia spp., Orthodes spp., Orthogonia spp., Orthosia spp., Oryzaephilus spp., Oscinella spp., *Oscinella frit*, Osminia spp., Ostrinia spp., *Ostrinia nubilalis*, Otiorhynchus spp., Ourapteryx spp., Pachetra spp., Pachysphinx spp., Pagyda spp., Paleacrita spp., Paliga spp., Paithis spp., Pammene spp., Pandemis spp., Panemeria spp., Panolis spp., *Panolis flammea*, Panonychus spp., Parargyresthia spp., Paradiarsia spp., Paralobesia spp., Paranthrene spp., Parapandemis spp., Parapediasia spp., Parastichtis spp., Parasyndemis spp., Paratoria spp., Pareromeme spp., Pectinophora spp., *Pectinophora gossypiella*, Pediculus spp., Pegomyia spp., *Pegomyia hyoscyami*, Pelochrista spp., Pennisetia spp., Penstemonia spp., Pemphigus spp., Peribatodes spp., Peridroma spp., Perileucoptera spp., Periplaneta spp., Perizoma spp., Petrova spp., Pexicopia spp., Phalonia spp., Phalonidia spp., Phaneta spp., Phlyctaenia spp., Phlyctinus spp., Phorbia spp., Phragmatobia spp., Phricanthes spp., Phthorimaea spp., *Phthorimaea operculella*, Phyllocnistis spp., Phyllocoptruta spp., *Phyllocoptruta oleivora*, Phyllonorycter spp., Phyllophila spp., Phylloxera spp., Pieris spp., *Pieris rapae*, Piesma spp., Planococus spp., Planotortrix spp., Platyedra spp., Platynota spp., Platyptilia spp., Platysenta spp., Plodia spp., Plusia spp., Plutella spp., *Plutella xylostelia*, Podosesia spp., Polia spp., Popillia spp., Polymixis spp., Polyphagotarsonemus spp., *Polyphagotarsonemus latus*, Prays spp., Prionoxystus spp., Probole spp., Proceras spp., Prochoerodes spp., Proeulia spp., Proschistis spp., Proselena spp., Proserpinus spp., Protagrotis spp., Proteoteras spp., Protobathra spp., Protoschinia spp., Pselnophorus spp., Pseudaletia spp., Pseudanthonomus spp., Pseudatemelia spp., Pseudaulacaspis spp., Pseudexentera spp., Pseudococus spp., Pseudohermenias spp., Pseudoplusia spp., Psoroptes spp., Psylta spp., Psylliodes spp., Pterophorus spp., Ptycholoma spp., Pulvinaria spp., *Pulvinaria aethiopica*, Pyralis spp., Pyrausta spp., Pyrgotis spp., Pyrreferra spp., Pyrrharctia spp., Quadraspidiotus spp., Rancora spp., Raphia spp., Reticultermes spp., Retinia spp., Rhagoletis spp, *Rhagoletis pomonella*, Rhipicephalus spp., Rhizoglyphus spp., Rhizopertha spp., Rhodnius spp., Rhophalosiphum spp., Rhopobota spp., Rhyacia spp., Rhyacionia spp., Rhynchopacha spp., Rhyzosthenes spp., Rivula spp., Rondotia spp., Rusidrina spp., Rynchaglaea spp., Sabulodes spp., Sahibergella spp., *Sahlbergella singularis*, Saissetia spp., Samia spp., Sannina spp., Sanninoidea spp., Saphoideus spp., Sarcoptes spp., Sathrobrota spp., Scarabeidae, Sceliodes spp., Schinia spp., Schistocerca spp., Schizaphis spp., Schizura spp., Schreckensteinia spp., Sciara spp., Scirpophaga spp., *Scirthrips auranti*, Scoparia spp., Scopula spp., Scotia spp., Scotinophara spp., Scotogramma spp., Scrobipalpa spp., Scrobipalpopsis spp., Semiothisa spp., Sereda spp., Sesamia spp., Sesia spp., Sicya spp., Sideridis spp., Simyra spp., Sineugraphe spp., Sitochroa spp., Sitobion spp., Sitophilus spp., Sitotroga spp., Solenopsis spp., Smerinthus spp., Sophronia spp., Spaelotis spp., Spargaloma spp., Sparganothis spp., Spatalistis spp., Sperchia spp., Sphecia spp., Sphinx spp., Spilonota spp., Spodoptera spp., *Spodoptera littoralis*, Stagmatophora spp., Staphylinochrous spp., Stathmopoda spp., Stenodes spp., Sterrha spp., Stomoxys spp., Strophedra spp., Sunira spp., Sutyna spp., Swammerdamia spp., Syllomatia spp., Sympistis spp., Synanthedon spp., Synaxis spp., Syncopacma spp., Syndemis spp., Syngrapha spp., Synthomeida spp., Tabanus spp., Taeniarchis spp., Taeniothrips spp., Tannia spp., Tarsonemus spp., Tegulifera spp., Tehama spp., Teleiodes spp., Telorta spp., Tenebrio spp., Tephrina spp., Teratoglaea spp., Terricula spp., Tethea spp., Tetranychus spp., Thalpophila spp., Thaumetopoea spp., Thiodia spp., Thrips spp., *Thrips palmi, Thrips tabaci*, Thyridopteryx spp., Thyris spp., Tineola spp., Tipula spp., Tortricidia spp., Tortrix spp., Trachea spp., Trialeurodes spp., *Trialeurodes vaporariorum*, Triatoma spp., Triaxomera spp., Tribolium spp., Tricodectes spp., Trichoplusia spp., *Trichoplusia ni*, Trichoptilus spp., Trioza spp., *Trioza erytreae*, Triphaenia spp., Triphosa spp., Trogoderma spp., Tyria spp., Udea spp., Unaspis spp., *Unaspis citri*, Utetheisa spp., Valeriodes spp., Vespa spp., Vespamima spp., Vitacea spp., Vitula spp., Witlesia spp., Xanthia spp., Xanthorhoe spp., Xanthotype spp., Xenomicta spp., Xenopsylla spp., *Xenopsylla cheopsis*, Xestia spp., Xylena spp., Xylomyges spp., Xyrosaris spp., Yponomeuta spp., Ypsolopha spp., Zale spp., Zanclognathus spp., Zeiraphera spp., Zenodoxus spp., Zeuzera spp., Zygaena spp., The good pesticidal activity of the compositions according to the invention correspond to a destruction rate (mortality) of at least 50–60% of the abovementioned pests, or of their eggs and larvae.

Behaviour-altering substances which are suitable for the invention are pheromones, kairomones and attractants, primarily pheromones. Such signal substances are effective even at extraordinarily low concentrations and are capable of altering the behaviour of the insects in a manner which allows their control. Pheromones are sexual signal substances produced in most cases by the female adults of the pests, primarily insects, which attract the male individuals of the same pest species. The natural pheromones are volatile and can display their attractant action over vast distances. The term "pheromone" may be used to describe not only a chemically defined individual compound, but also a mixture of compounds. It depends on the species whether it means a defined individual compound or a mixture of compounds. Suitable for the purposes of the invention are, in principle, all pheromones which have been described in the literature.

The compositions according to the invention comprise the behaviour-altering substance preferably in an amount of from 0.01 to 10% by weight, in particular 0.02 to 5% by weight, very especially 0.04 to 2%. Most especially preferred is a pheromone content of 0.08 to 0.24% by weight for controlling the eggs of representatives of the order Lepidoptera, and a pheromone content of from 0.7 to 0.9% by weight for controlling the eggs of representatives of the order Coleoptera. A typical pheromone content for controlling the eggs of representatives of the order Lepidoptera is 0.16% by weight, and for controlling the eggs of representatives of the order Coleoptera 0.8% by weight. Also preferred is a composition which comprises only one pheromone. In the case of kairomones and attractants, which are mostly used in compositions for controlling larval stages, amounts of from 0.5 to 30% by weight, especially 5 to 20% by weight, are employed.

Structure and composition of the pheromones are known from the literature. Examples of pheromones which can be used within the scope of the present invention are the following:

Z-5-decenyl acetate, dodecanyl acetate, Z-7-dodecenyl acetate, E-7-dodecenyl acetate, Z-8-dodecenyl acetate, E-8-dodecenyl acetate, Z-9-dodecenyl acetate, E-9-dodecenyl acetate, E-10-dodecenyl acetate, 11-dodecenyl acetate, Z-9,11-dodecadienyl acetate, E-9,11-dodecadienyl acetate, Z-11-tridecenyl acetate, E-11-tridecenyl acetate, tetradecanyl acetate, E-7-tetradecenyl acetate, Z-8-tetradecenyl acetate, E-8-tetradecenyl acetate, Z-9-tetradecenyl acetate, E-9-tetradecenyl acetate, Z-10-tetradecenyl acetate, E-10-tetradecenyl acetate, Z-11-tetradecenyl acetate, E-11-tetradecenyl acetate, Z-12-pentadecenyl acetate, E-12-pentadecenyl acetate, hexadecanyl acetate, Z-7-hexadecenyl acetate, Z-11-hexadecenyl acetate, E-11-hexadecenyl acetate, octadecanyl acetate, E,Z-7,9-dodecadienyl acetate, Z,E-7,9-dodecadienyl acetate, E,E-7,9-dodecadienyl acetate, Z,Z-7,9-dodecadienyl acetate, E,E-8,10-dodecadienyl acetate, E,Z-9,12-dodecadienyl acetate, E,Z-4,7-tridecadienyl acetate, 4-methoxy-cinnamaldehyde-β-ionone, estragol (4-allylanisole), eugenol (4-allyl-2-methoxyphenol), indole, 8-methyl-2-decyl propanoate, E,E-9,11-tetradecadienyl acetate, Z,Z-9,12-tetradecadienyl acetate, Z,Z-7,11-hexadecadienyl acetate, E,Z-7,11-hexadecadienyl acetate, Z,E-7,11-hexadecadienyl acetate, E,E-7,11-hexadecadienyl acetate, Z,E-3,13-octadecadienyl acetate, E,Z-3,13-octadecadienyl acetate, E,E-3,13-octadecadienyl acetate, ethanol, hexanol, heptanol, octanol, decanol, Z-6-nonenol, E-6-nonenol, dodecanol, 11-dodecenol, Z-7-dodecenol, E-7-dodecenol, Z-8-dodecenol, E-8-dodecenol, E-9-dodecenol, Z-9-dodecenol, E-9,11-dodecadienol, Z-9,11-dodecadienol, Z,E-5,7-dodecadienol, E,E-5,7-dodecadienol, E,E-8,10-dodecadien-1-ol (codlemone, codlure), E,Z-8,10-dodecadienol, Z,Z-8,10-dodecadienol, Z,E-8,10-dodecadienol, E,Z-7,9-dodecadienol, Z,Z-7,9-dodecadienol, E-5-tetradecenol, Z-8-tetradecenol, Z-9-tetradecenol, E-9-tetradecenol, Z-10-tetradecenol, Z-11-tetradecenol, E-11-tetradecenol, Z-11-hexadecenol, Z,E-9,11-tetradecadienol, Z,E-9,12-tetradecadienol, Z,Z-9,12-tetradecadienol, Z,Z-10,12-tetradecadienol, Z,Z-7,11-hexadecadienol, Z, E-7,11-hexadecadienol, (E)-14-methyl-8-hexadecen-1-ol, (Z)-14-methyl-8-hexadecen-1-ol, E,E-10,12-hexadecadienol, E,Z-10,12-hexadecadienol, dodecanal, Z-9-dodecenal tetradecanal, Z-7-tetradecenal, Z-9-tetradecenal, Z-11-tetradecenal, E-11-tetradecenal, E-11,13-tetradecadienal, E,E-8,10-tetradecadienal, Z,E-9,11-tetradecadienal, Z,E-9,12-tetradecadienal hexadecanal, Z-8-hexadecenal, Z-9-hexadecenal, Z-10-hexadecenal, E-10-hexadecenal, Z-11-hexadecenal, E-11-hexadecenal, Z-12-hexadecenal, Z-13-hexadecenal (Z)-14-methyl-8-hexadecenal (E)-14-methyl-8-hexadecenal-Z,Z-7,11-hexadecadienal, Z,E-7,11-hexadecadienal, Z,E-9,11-hexadecadienal, E,E-10,12-hexadecadienal, E,Z-10,12-hexadecadienal, Z,E-10,12-hexadecadienal, Z,Z-10,12-hexadecadienal, Z,Z-11,13-hexadecadienal octadecanal, Z-11-octadecenal, E-13-octadecenal, Z-13-octadecenal, Z-5-decenyl-3-methyl butanoate.

| | |
|---|---|
| disparlure: | (+)cis-7,8-epoxy-2-methyloctadecane |
| seudenol | 3-methyl-2-cyclohexen-1-ol |
| sulcatol: | 6-methyl-5-hepten-2-ol |
| ipsenol: | 2-methyl-6-methylene-7-octen-4-ol |

-continued

| | |
|---|---|
| ipsdienol: | 2-methyl-6-methylene-2,7-octadien-4-ol |
| grandlure I: | cis-2-isopropenyl-1-methylcyclobutane-ethanol |
| grandlure II: | Z-3,3,-dimethyl-1-cyclohexane-ethanol |
| grandlure III: | Z-3,3,-dimethyl-1-cyclohexane-acetaldehyde |
| grandlure IV: | E-3,3,-dimethyl-1-cyclohexane-acetaldehyde |
| cis-2-verbenol: | cis-4,6,6-trimethylbicyclo[3.1.1]hept-3-en-2-olcucurbitacin |
| | 2-methyl-3-buten-2-ol |
| | 4-methyl-3-heptanol |
| cucurbitacin | 2-methyl-3-buten-2-ol |
| | 4-methyl-3-heptanol |
| α-pinene: | 2,6,6-trimethylbicyclo[3.1.1]hept-2-ene |
| α-caryophyllene: | 4,11,11-trimethyl-8-methylenebicyclo[7.2.0]undecane |
| | Z-9-tricosene |
| α-multistriatin | 2(2-endo,4-endo)-5-ethyl-2,4-dimethyl-6,8-dioxabicyclo-[3.2.1]octane |
| methyleugenol: | 1,2-dimethoxy-4-(2-propenyl)phenyl |
| lineatin: | 3,3,7-trimethyl-2,9-dioxatricyclo[3.3.1.0]nonane |
| chalcogran: | 2-ethyl-1-6-dioxaspiro[4.4]nonane |
| frontalin: | 1,5-dimethyl-6,8-dioxabicyclo[3.2.1]octane |
| endo-brevicomin: | endo-7-ethyl-5-methyl-6,8-dioxabicyclo[3.2.1]octane |
| exo-brevicomin: | exo-7-ethyl-5-methyl-6,8-dioxabicyclo[3.2.1]octane |
| | (Z)-5-(1-decenyl)dihydro-2(3H)-furanone |
| farnesol | 3,7-,11-trimethyl-2,6,10-dodecatrien-1-ol |
| nerolidol | 3,7-,11-trimethyl-1,6,10-dodecatrien-3-ol |
| | 3-methyl-6-(1-methylethenyl)-9-decen-1-ol acetate |
| | (Z)-3-methyl-6-(1-methylethenyl)-3,9-decadien-1-ol acetate |
| | (E)-3,9-methyl-6-(1-methylethenyl)-5,8-decadien-1-ol acetate |
| | 3-methylene-7-methylocten-1-ol propionate |
| | (Z)-3,7-dimethyl-2,7-octadien-1-ol propionate |
| | (Z)-3,9-dimethyl-6-(1-methylethenyl)-3,9-decadien-1-ol propionate |

Kairomones are also naturally occurring signal substances. They are produced by plants and consist in most cases of a mixture of a multiplicity of various volatile odouriferous substances. The kairomones are capable of attracting insects and representatives of the order Acarina. However, repellent effects are also possible, depending on the concentration. The activity of the kairomones must be seen in context with the fact that insects and Acarina live in close symbiosis with the plants in question.

The so-called attractants are known chemical compounds which are relatively readily available and which are capable of affecting the behaviour of pests in the sense that the pests are made accessible and exposed in especially high degree to the action of pesticides which are simultaneously present.

Such kairomones and attractants, which can also be used for the purposes of the invention—preferably in combination with pheromones—are also known from the literature.

Naturally, the pesticidally active compounds employed in the compositions and products according to the invention must be compatible with the remaining constituents of the composition according to the invention and at least mostly soluble therein. Nor must the pesticidally active ingredients evaporate too rapidly; rather they must be present in or on the surface of the microdrop or drop-shaped zones for an adequate period so as to allow uptake of the active ingredient by the pest to be controlled. The compositions according to the invention preferably comprise 1 to 15% by weight, especially 5 to 12% by weight, of the pesticidally active compound. A typical content of pesticidally active compound is 10% by weight. Preferred is a composition which comprises only one pesticidally active compound.

A flowable composition for the purposes of the invention is a composition which typically shows flow characteristics like honey or glue, for example. Compositions with better flowability can be employed so long as they adhere well to the support, for example the leaf or the bark of the plant. The viscosity of the composition according to the invention is preferably within a range of from 1000 to 40 000, especially 10 000 to 30 000, in particular 15 000 to 25 000 cP (centipoise). A typical viscosity is 20 000 cP.

The viscosities of the compositions according to the invention are normally determined using a method in which the torque required to overcome the resistance of a fluid, due to its viscosity, to the rotatory movement of a cylinder or disc is measured by means of the tension of a metal spring (so-called torsion principle). The tension of the spring shown (torque) is proportional to the viscosity, which is given in millipascal seconds (mPa s=1 cP). The measurements are carried out for example using a Brookfield Synchro-Lectric viscometer, model LV, from Brookfield Engineering Laboratories Inc., Stoughton, Mass., USA.

The term UV absorber is to be understood as meaning, in accordance with the invention, a compound which has a main absorption range of between 200 and 450 nm, especially between 270 and 400 nm. In most cases, these are the known commercially available UV absorbers which are known in particular from the plastics industry. Compounds which are preferably employed are those belonging to the following classes of substances: benzotriazole derivatives, benzophenone derivatives, cinnamic acid derivatives, oxalanilides, sterically hindered amines, in particular piperidine derivatives, and triazines. The benzotriazole derivatives are especially preferred. If appropriate, other substances which are not normally termed UV absorbers in the narrow sense may be used for this purpose provided they are sufficiently stable to light, have a sufficiently high absorption in the abovementioned absorption range and are capable of being processed together with the remaining components to give a composition with the desired viscosity. Sterically hindered amines, especially piperidine derivatives, are mentioned in the present context amongst the UV absorbers even though their mode of action is probably due to their antioxidant characteristics. In the event that they are employed, they are preferably not employed alone, but in combination with one or more substances from one of the other classes of UV absorbers mentioned, especially in combination with benzotriazoles, preferably in an amount of 5 to 10% by weight relative to the entire composition.

Especially preferred is a composition which comprises 50 to 95% by weight, especially 60 to 90%, in particular 70 to 90%, especially preferably 80 to 90%, of the UV absorber or UV absorber mixture known per se. A typical content is 85% by weight. Also preferred is a composition which comprises only one UV absorber. Preferably used are liquid or flowable UV absorbers with a cP value of between 1000 and 40 000, especially between 10 000 and 30 000. On the other hand, it is also possible to use one or more solid UV absorbers and to convert them, with or without other auxiliaries, for example solvents, into the desired flowable form. It is also possible to mix a flowable UV absorber with a solid UV absorber—again, with or without further auxiliaries—to convert the composition into the desired flowable form.

Examples of sub-groups of UV absorbers and free-radical scavengers of the abovementioned classes which are especially suitable in accordance with the invention are:

A) 2-(2-Hydroxyphenyl)benzotriazoles of the formula

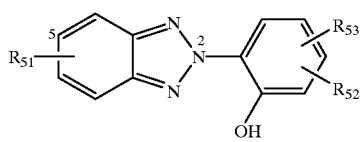

(VI)

in which $R_{51}$ is H or halogen, especially H or Cl; very especially H or 5—Cl $R_{52}$ is H, $C_1$–$C_{18}$alkyl, phenyl-$C_1$–$C_{12}$alkyl, phenyl; especially $C_1$–$C_{12}$alkyl, $R_{53}$ is H, $C_1$–$C_{18}$alkyl, phenyl-$C_1$–$C_{12}$alkyl, phenyl, —$(CH_2)_g$—COO—$C_1$–$C_{12}$alkyl, —$(CH_2)_h$—COO—$C_1$–$C_{24}$alkenyl; and g and h independently of one another are 1 to 20, especially 2; or $R_{53}$ is a chain formed by reacting a compound of the formula (VI), in which $R_{53}$ is a radical —$(CH_2)_g$—COO—$C_1$–$C_{12}$alkyl with a polyethyleneglycol.

Especially preferred compounds of the formula (VI) are:

the reaction product of

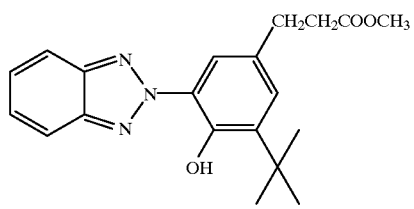

and $HO(CH_2CH_2O)_iH$ (polyethylene glycol 300, i=6 or 7, mean molecular weight of the reaction product>600, known under the tradename Tinuvin 1130);

the reaction product formed by alkylating 2-(2-hydroxy-5-methylphenyl)benzotriazole with i-dodecene:

(Tinuvin 171)

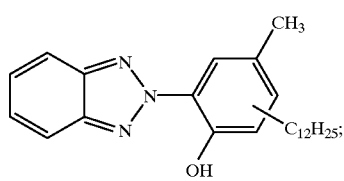

2-(2'-hydroxy-3'-tert-butyl-5'-methylphenyl)-5-chlorobenzotriazole (Tinuvin 326);

2-(2'-hydroxy-3',5'-di-tert-butylphenyl)-5-chlorobenzotriazole (Tinuvin 327);

2-(2'-hydroxy-3',5'-di-tert-amylphenyl)benzotriazole (Tinuvin 328);

2-(2'-hydroxy-3',5'-di-tert-butylphenyl)-5-chlorobenzotriazole (Tinuvin 329); and the compound of the formula

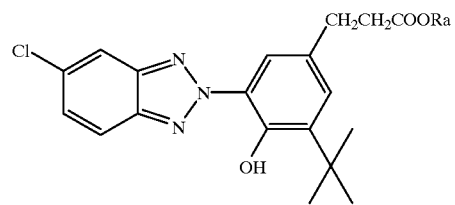

in which $R_a$ is $C_4$–$C_{18}$alkyl, especially $C_8$alkyl, very especially a compound in which $R_a$ is composed of approximately 50% n-octyl and approximately 50% 2-ethylhexyl (Tinuvin 109);

B) 2-hydroxy-4-alkoxybenzophenones of the formula

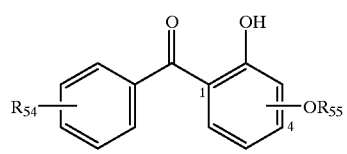

(VII)

in which $R_{54}$=H, $C_1$–$C_{18}$alkyl, $C_1$–$C_{18}$alkoxy $R_{55}$=$C_1$–$C_{18}$alkyl, preferably —$C_8H_{17}$ and —$C_{12}H_{25}$, especially the compound of the formula (VII), in which $R_{54}$ is hydrogen and —$OR_{55}$ is 4-O-n-$C_8H_{17}$ (Chimassorb 81);

C) oxalanilides of the formula

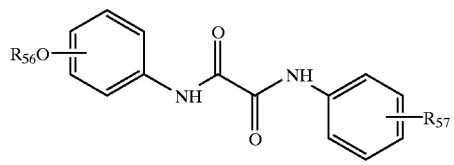

(VIII)

in which $R_{56}$ is $C_1$–$C_{18}$alkyl and $R_{57}$ is $C_1$–$C_{18}$alkyl;

D) cinnamic acid derivatives of the formula

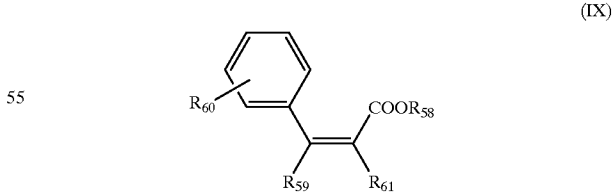

(IX)

in which $R_{58}$ is H or $C_1$–$C_{18}$alkyl;

$R_{59}$ is H or $C_1$–$C_6$alkyl or phenyl;

$R_{60}$ is H or $C_1$–$C_{18}$alkoxy and $R_{61}$ is H, CN or COO-$C_1$–$C_{18}$alkyl;

in free form or in salt form;

E) triazine derivatives of the formula (X)

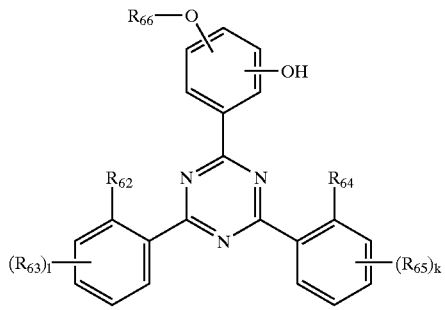

in which $R_{62}$ and $R_{64}$ independently of one another are H, $C_1$–$C_{12}$alkyl or OH;

$R_{63}$ and $R_{65}$ independently of one another are $C_1$–$C_{18}$alkyl or $C_1$–$C_{18}$alkoxy;

$R_{66}$ is $C_1$–$C_{18}$alkyl; $C_1$–$C_{18}$alkoxy-$C_1$–$C_{12}$alkyl, $C_1$–$C_{18}$alkoxyhydroxy-$C_1$–$C_{12}$alkyl;

k is 0, 1 or 2 and l is 0, 1 or 2;

where, if k and/or l are 2, the radicals $R_{63}$ and $R_{65}$ are independent of one another;

in free form or in salt form;

especially a mixture of 2-[4-((2-hydroxy-3-didecyloxypropyl)-oxy]-2-hydroxyphenyl]-4,6-bis(2,4-dimethylphenyl)-1,3,5-triazine and 2-[4-((2-hydroxy-3-tridecyloxypropyl)-oxy]-2-hydroxyphenyl]-4,6-bis(2,4-dimethylphenyl)-1,3,5-triazine, with an approximate molecular weight of 654 (Tinuvin 400);

F) piperidine derivatives of the formula (XI)

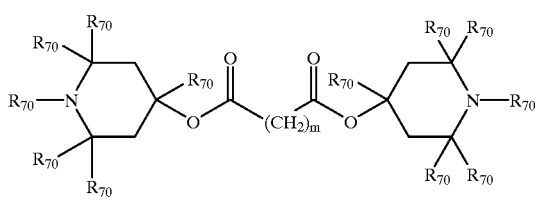

in which the radicals $R_{70}$ independently of one another are hydrogen or $C_1$–$C_4$alkyl, especially hydrogen or methyl, and m is 2 to 8, especially 8, in free form or in salt form;

especially bis-2,2,6,6-tetramethyl-4-piperidyl sebacate (Tinuvin 770 DF) and bis-1,2,2,6,6-pentamethyl-4-piperidyl sebacate (Tinuvin 765);

G) piperidine derivatives of the formula (XII)

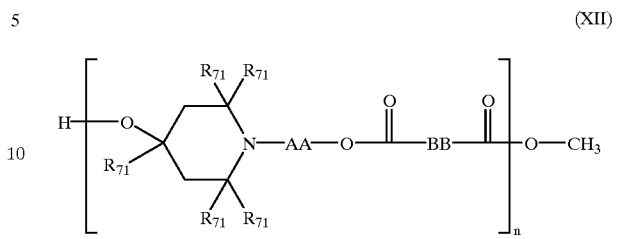

in which the radicals $R_{71}$ independently of one another are hydrogen or $C_1$–$C_4$alkyl, especially hydrogen or methyl, AA and BB independently of one another are $C_1$–$C_8$alkylene, especially —$CH_2$—$CH_2$—, and n is sufficiently large that the molecular weight of the compound is between 1000 and 4000;

in free form or in salt form;

especially poly-(N-β-hydroxyethyl-2,2,6,6-tetramethyl-4-hydroxypiperidyl succinate (Tinuvin 622 LD);

and the compounds n-butylamine-nickel 2,2'-thiobis(4-tert-octylphenolate) (Chimassorb N-705), and poly-{[6-[(1,1,3,3-tetramethylbutyl)imino]-1,3,5-triazine-2,4-diyl][2-(2,2,6,6-tetramethylpiperidyl)amino] hexamethylene-[4-(2,2,6,6-tetramethylpiperidyl)imino]} (Chimassorb 944 LD/FL).

If required, the flowable products according to the invention may comprise customary viscosity-regulating thickeners in an amount of from 1 to 47% by weight, preferably in an amount of from 1 to 20% by weight. Examples of suitable organic thickeners are: base-neutralized acrylic acid polymers of high molecular weight and relatively high viscosity ("Carbpole" types), polyvinylpyrrolidones, cellulose gums, in particular cellulose alkyl esters and cellulose alkyl ethers ("Blanose" types), liquid polyalkylene glycol block copolymers of ethylene oxide and propylene oxide ("Pluronic" types), polyethylene glycols with a molecular weight of above 10 000, and polyisobutylene with a molecular weight of approximately 1000 (Glissopal 1000). Amongst the inorganic thickeners, the following may be mentioned, for example: precipitated or pyrogenic silicas, aluminas and rock meals, in particular calcite, various types of talcum, or kaolins, bentonites, montmorillonites, smectites and attapulgite, aluminalsilica ("Aerosil" types) and sodium aluminium silicates. Quartz sand or crosslinked solid pulverulent polymers may be incorporated into the products as additional fillers.

To modify the viscosity of the flowable products according to the invention, it may be expedient in certain cases to add an inert solvent or diluent. These solvents should be compatible with the remaining constituents of the product and, preferably, of low volatility. Suitable examples are the following solvents: ethers and ether-like compounds of low volatility such as dipropyl ether, dibutyl ether, dioxane, dimethoxyethane and tetrahydrofuran; N,N-dialkylated carboxamides; aliphatic, aromatic and halogenated hydrocarbons, in particular pentanes, hexanes, heptanes, octanes, hexadecane, toluene, xylenes, chlorohydrocarbons and chlorobenzenes, alcohols, such as ethanol, propanols, t-butanol and higher alcohols; nitriles, such as acetonitrile or propionitrile; and ketones, for example methyl isopropyl ketone and methyl isobutyl ketone; alkyl esters of aliphatic carboxylic acids, such as butyl propionate, methyl oxalate, dibutyl sebacate, di(2-ethylhexyl) sebacate. In general, the formulations according to the invention only comprise relatively small amounts of solvents, for example 1 to 2% by weight.

If required, the compositions according to the invention can furthermore comprise other formulation auxiliaries which serve to adapt the composition to specific conditions or which protect the biological active ingredients which they comprise against certain environmental factors. Such formulation auxiliaries can be substances which provide an additional protection against UV, such as finely divided carbon powders (e.g. pigment-grade carbon black), dyes and colour pigments (e.g. Sudan black, Chromophthal blue, Terasil blue, Cibacet yellow, titanium dioxide, zinc sulfate and zinc oxides), optical brighteners (e.g. Uvitex or Tinopal DMS), antioxidants (e.g. butylhydroxytoluene or 2,6-di-tert-butyl-p-cresol) and, in some cases, also specific surfactants and emulsifiers (e.g. anionic surfactants: sodium lauryl sulfate, calcium dodecylbenzenesulfonate, and non-ionic surfactants: fatty alcohol ethoxylates, alkylphenol ethoxylates, oleyl alcohol ethoxylates, ethylene oxide/propylene oxide block copolymers, fatty amine ethoxylates, silicone surfactants). Lime pigments and colour pigments may amount to 1 to 20% by weight, preferably 3 to 10% by weight, of the compositions according to the invention, optical brighteners to 0.1 to 2% by weight, antioxidants to 0.1 to 5% by weight, and surfactants and emulsifiers to 0.1 to 1% by weight.

Within the scope of the method according to the invention for controlling plant-injurious insects and representatives of the order Acarina, the compositions according to the invention are generally not distributed over the agriculturally cultivated area by using conventional devices as they are known to the expert, since said conventional methods ire more suitable for spraying compositions of low viscosity, for example aqueous emulsions or suspensions. Rather, methods which have proved successful are, for example, automatic pipettes with suitable dosing devices by means of which individual microdrops or drop-shaped zones are applied. Also suitable are devices with intermittent drop delivery which is controlled by pressurized air or mechanically, and these devices are mainly suitable for larger areas. The microdrops are applied directly to the plants or to a suitable location in the vicinity of the plants, preferably to the plants, for example to the leaves or bark, preferably to the leaves. The number of microdrops or drop-shaped zones distributed over the cultivated area to be treated may differ within the scope of the present invention, depending on the species of the pests to be controlled and their developmental stages. 50 up to 100 000 microdrops or drop-shaped zones may be distributed per 1000 m$^2$ of the cultivateded area to be protected, and 100 to 1500, especially 200 to 500, microdrops or drop-shaped zones of the composition according to the invention are generally distributed. The size of the microdrops applied is preferably 5 to 3000 µl, in particular 30 to 1000 µl, especially 30 to 200 µl, typically 50 µl.

In the following examples which illustrate the invention, parts and percentages are by weight, unless stated otherwise:

EXAMPLE 1

A flowable formulation with a viscosity of 25 000 cP is prepared by intimately mixing the following constituents (formulation A):

| | |
|---|---|
| Tinuvin 171 (cf. above information) | 68.64% |
| Glissopal 1000 (polyisobutylene, molecular weight approximately 1000) | 10% |
| Diofenolan | 10% |
| Codlemon | 0.16% |
| Neptune black X60 (disazo dye) | 4% |
| Neptune black (Spezialschwarz) 5 (amorphous carbon) | 4% |
| Aerosil COK 84 (finely divided SiO$_2$/Al$_2$O$_3$ - 84:16% by weight) | 3.2% |

The following flowable formulation is prepared analogously (formulation B):

| | |
|---|---|
| Tinuvin 171 | 68.64% |
| Glissopal 1000 (polyisobutylene, molecular weight approximately 1000) | 10% |
| Fenoxycarb | 10% |
| Codlemon | 0.16% |
| Neptune black (Neptun Schwarz) X60 (disazo dye) | 4% |
| Special black (Spezialschwarz) 5 (amorphous carbon) | 4% |
| Aerosil COK 84 | 3.2% |

Drops of in each case 100 µl of these formulations are applied to an aluminium foil and each day exposed to UV irradiation (UV lamp) for 9 hours at 35° C., alternating with 15 hours in the dark at a temperature of 12° C. Immediately after this treatment, drops which have been treated over different periods are tested in a wind tunnel for insecticidal activity against, and attractant effect on, males of *Cydia pomonella*.

The wind tunnel used is described in EP-A-376 888. Essentially, it consists of a sealed channel of transparent material with a rectangular cross-section. A drop of the attractant/insecticide formulation as described above is applied at one end of the channel. Short open glass tubes accommodating the insects and a starting platform are arranged at the opposite end of the channel. From this starting platform, the pest flies straight to the source of the attractant (i.e. the drop comprising the active ingredient). For each flying test, the glass tube is populated with one pest. On average, 40 flying tests are carried out per test formulation. The male pests which have touched the source which comprises the pesticide are subsequently kept in a container together with females of the same species which have not come into contact with the pesticide. The number of larvae hatching from the eggs deposited by females which have thus been kept is determined and compared with the hatching rate of eggs which have been deposited by females kept together with males which had not come into contact with insecticide (% sterilization). The abovementioned formulations A and B are tested using *Cydia pomonella* adults 2 to 3 days old.

TABLE

Sterilization of Cydia pomonella eggs

| Formulation A | | Formulation B | | No contact with pesticide | |
|---|---|---|---|---|---|
| No. of eggs | Sterilization % | No. of eggs | Sterilization % | No. of eggs | Sterilization % |
| 2097 | 96 | 1230 | 85 | 1465 | 39 |
| 1750 | 96 | 1445 | 85 | 938 | 50 |
| 1653 | 93 | 1866 | 85 | 2365 | 39 |
| 1537 | 89 | 1784 | 89 | 2182 | 33 |
| 1629 | 81 | 1602 | 80 | 1065 | 24 |
| Total: 8666 | Average: 91% | Total: 7927 | Average: 85% | Total: 8015 | Average: 33% |

EXAMPLES 2 TO 28

Viscous formulations are prepared analogously to Example 1 using the following constituents:

| No. | Component | % by weight |
|---|---|---|
| 2 | Tinuvin 171 | 80.1% |
| | Tinuvin 765 | 1.6% |
| | Aerosil COK 84 (finely divided SiO$_2$/Al$_2$O$_3$ - 84:16% by weight) | 3.2% |
| | Carbon powder (particle size 20 nm) | 4.0% |
| | Sudan black B | 4.0% |
| | Fonoxycarb | 4.0% |
| | Hexane | 2.9% |
| | Pheromone | 0.2% |

Composition of the pheromone used in parts by weight: (Z)9-tetradecenyl acetate: 9, (Z)11-tetradecanyl acetate: 1, (Z)9-tetradecenol: 1, (Z)11-tetradecenol: 0.2

The finished formulation is tested in the wind tunnel against *Eupoecilia ambiguella* males in accordance with the protocol described in Example 1, and the hatching rates of treated and untreated eggs are compared. In this test, the formulation has a good activity.

| No. | Component | % by weight |
|---|---|---|
| 3 | Tinuvin 171 | 81.2% |
| | Aerosil COK 84 | 3.2% |
| | Pigment-grade carbon black | 4.0% |
| | Sudan black B | 4.0% |
| | Imidacloprid | 4.5% |
| | Hexane | 3.0% |
| | Pheromone | 0.1% |

Composition of the pheromone used in parts by weight: (Z)9-tetradecenyl acetate: 9, (Z)11-tetradecanyl acetate: 1, (Z)9-tetradecenol: 1, (Z)11-tetradecenol: 0.2

| No. | Component | % by weight |
|---|---|---|
| 4 | Tinuvin 171 | 83.6% |
| | Aerosil COK 84 | 3.2% |
| | Pigment-grade carbon black | 4.2% |
| | Sudan black B | 4.2% |
| | Puriproxyfen | 4.2% |
| | Hexane | 0.4% |
| | Pheromone | 0.2% |

Composition of the pheromone used in Examples 3 and 4 in parts by weight: Z,Z-7,11-hexadecadienyl acetate: 1, Z,E-7,11-hexadecadienyl acetate: 1.

| No. | Component | % by weight |
|---|---|---|
| 5 | Tinuvin 171 | 85.4% |
| | Aerosil COK 84 | 3.4% |
| | Pigment-grade carbon black | 4.3% |
| | Sudan black B | 4.3% |
| | (E)-N-(2-Chlorothiazol-5-ylmenthyl)-N-ethyl-N'-methyl-2-nitrovinylidenediamine | 0.9% |
| | Hexane | 1.5% |
| | Pheromone | 0.2% |

Composition of the pheromone used in parts by weight: (+)cis-2-isopropenyl-1-methylcyclobutane-ethanol: 40, (Z)-3,3-dimethyl-Δ-1,β-cyclohexane-ethanol: 30, (Z)-3,3-dimethyl-Δ-1,α-cyclohexane acetaldehyde: 15, (E)-3,3-dimethyl-Δ-1,α-cyclohexane acetaldehyde: 15

| No. | Component | % by weight |
|---|---|---|
| 6 | Tinuvin 171 | 83.7% |
| | Aerosil COK 84 | 3.4% |
| | Pigment-grade carbon black | 4.3% |
| | Sudan black B | 4.3% |
| | Pymetrozine | 2.7% |
| | Hexane | 1.5% |
| | 8-Methyl-2-decanol propanoate (pheromone) | 0.1% |
| 7 | Tinuvin 329 | 55.4% |
| | Aerosil COK 84 | 3.4% |
| | Pigment-grade carbon black | 4.3% |
| | Sudan black B | 4.3% |
| | Diafenthiuron | 0.9% |
| | Hexane | 31.5% |
| | Estragol | 0.1% |
| | 4-Methoxycinnamaldehyde (pheromone) | 0.1% |
| 8 | Tinuvin 171 | 89.7% |
| | Aerosil COK 84 | 4.0% |
| | Diofenolan | 4.0% |
| | Erythrosin (dye) | 1.0% |
| | Codlemon | 0.1% |
| | Hexane | 1.2% |
| 9 | Tinuvin 171 | 78.3% |
| | Glissopal 1000 | 10% |
| | Tebufenozide | 0.5% |
| | Neptune black (Neptun Schwarz) | 4% |
| | Special black (Spezial Schwarz) | 4% |
| | Aerosil COK 84 | 3.2% |
| 10 | Tinuvin 109 | 58.49% |
| | Glissopal 1000 | 20% |
| | Methoprene | 10% |
| | Neptune black (Neptun Schwarz) | 4% |
| | Special black (Spezial Schwarz) | 4% |
| | Codlemon | 0.16% |
| | Aerosil COK 84 | 3.35% |
| 11 | Tinuvin 171 | 63.49% |
| | Glissopal 1000 | 20% |
| | Methoprene | 5% |
| | Neptune black (Neptun Schwarz) | 4% |
| | Special black (Spezial Schwarz) | 4% |
| | 4-Methoxycinnamaldehyde (pheromone) | 0.16% |

-continued

| | | |
|---|---|---|
| | Aerosil COK 84 | 3.35% |
| 12 | Tinuvin 400 | 67.99% |
| | Glissopal 1000 | 20% |
| | Fenoxycarb | 0.5% |
| | Neptune black (Neptun Schwarz) | 4% |
| | Special black (Spezial Schwarz) | 4% |
| | Codlemon | 0.16% |
| | Aerosil COK 84 | 3.35% |
| 13 | Tinuvin 171 | 52.49% |
| | Glissopal 1000 | 21% |
| | Pyriproxyfen | 15% |
| | Neptune black (Neptun Schwarz) | 4% |
| | Special black (Spezial Schwarz) | 4% |
| | E-10-Hexadecenal (pheromone) | 0.16% |
| | Aerosil COK 84 | 3.35% |
| 14 | Tinuvin 328 | 40% |
| | Glissopal 1000 | 40% |
| | Fenoxycarb | 11.49% |
| | Neptune black (Neptun Schwarz) | 4% |
| | Special black (Spezial Schwarz) | 4% |
| | Codlemon | 0.16% |
| | Aerosil COK 84 | 0.35% |
| 15 | Tinuvin 109 | 68.72% |
| | Glissopal 1000 | 18% |
| | Fenoxycarb | 2% |
| | Neptune black (Neptun Schwarz) | 4% |
| | Special black (Spezial Schwarz) | 4% |
| | Codlemon | 0.08% |
| | Aerosil COK 84 | 3.2% |
| 16 | Tinuvin 400 | 97% |
| | Glissopal 1000 | 1% |
| | Fenoxycarb | 1% |
| | Codlemon | 0.08% |
| | Aerosil COK 84 | 0.92% |
| 17 | Tinuvin 109 | 92.07% |
| | Fenoxycarb | 0.5% |
| | Special black (Spezial Schwarz) | 4% |
| | Codlemon | 0.08% |
| | Aerosil COK 84 | 3.35% |
| 18 | Tinuvin 171 | 23.54% |
| | Tinuvin 400 | 54.94% |
| | Kinoprene | 10% |
| | Codlemon | 0.16% |
| | Neptune black (Neptun Schwarz) | 4% |
| | Special black (Spezial Schwarz) | 4% |
| | Aerosil COK 84 | 3.36% |
| 19 | Tinuvin 1130 | 47.2% |
| | Tinuvin 400 | 39.2% |
| | Diofenolan | 10% |
| | Codlemon | 0.16% |
| | Aerosil COK 84 | 3.44% |
| 20 | Tinuvin 171 | 44% |
| | Tinuvin 400 | 48% |
| | Fenoxycarb | 0.5% |
| | Codlemon | 0.16% |
| | Special black (Spezial Schwarz) | 4% |
| | Aerosil COK 84 | 3.34% |
| 21 | Tinuvin 171 | 17.6% |
| | Tinuvin 400 | 70.4% |
| | Tebufenozide | 0.5% |
| | 8-Methyl-2-decanol propanoate (pheromone) | 0.12% |
| | Neptune black (Neptun Schwartz) | 4% |
| | Special black (Spezial Schwarz) | 4% |
| | Aerosil COK 84 | 3.38% |
| 22 | Tinuvin 171 | 15.6% |
| | Tinuvin 400 | 62.4% |
| | Glissopal 1000 | 10% |
| | Pyriproxyfen | 0.5% |
| | Codlemon | 0.15% |
| | Neptune black (Neptun Schwarz) | 4% |
| | Special black (Spezial Schwarz) | 4% |
| | Aerosil COK 84 | 3.35% |
| 23 | Tinuvin 326 | 46% |
| | Glissopal 1000 | 16% |
| | Diofenolan | 8% |
| | Codlemon | 0.2% |
| | Aerosil COK 84 | 1.8% |
| | Toluene | 28% |
| 24 | Tinuvin 171 | 78.49% |
| | Glissopal 1000 | 5% |
| | Kinoprene | 5% |
| | Neptune black (Neptun Schwarz) | 4% |
| | Special black (Spezial Schwarz) | 4% |
| | Codlemon | 0.10% |
| | Aerosil COK 84 | 3.41% |
| 25 | Tinuvin 171 | 62% |
| | Glissopal 1000 | 26% |
| | Diofenolan | 0.5% |
| | Neptune black (Neptun Schwarz) | 4% |
| | Special black (Spezial Schwarz) | 4% |
| | (+)cis-7,8-Epoxy-2-methyloctadecane (pheromone) | 0.25% |
| | Aerosil COK 84 | 3.25% |
| 26 | Tinuvin 400 | 89% |
| | Tinuvin 770 DF | 1.2% |
| | Aerosil COK 84 | 4.1% |
| | Tebufenozide | 4.5% |
| | 8-Methyl-2-decanol propanoate (pheromone) | 0.1% |
| | Dibutyl sebacate | 1.1% |
| 27 | Tinuvin 1130 | 84.9% |
| | Aerosil COK 84 | 4.2% |
| | Carbon powder | 4.2% |
| | Acetamiprid | 4.2% |
| | Codlemon | 0.1% |
| | Ethanol | 2.4% |
| 28 | Tinuvin 1130 | 80.9% |
| | Aerosil COK 84 | 3.6% |
| | Carbon powder | 4.0% |
| | Sudan black B | 4.0% |
| | Nitenpyram | 4.0% |
| | Codlemon | 0.1% |
| | Ethanol | 3.4% |

What is claimed is:

1. A method of controlling eggs of harmful insects and representatives of the order Acarina, which comprises distributing to the areas to be protected, a composition comprising:

at least one pesticidally active compound, one or more signal substances selected from the group consisting of pheromones, kairomones or attractants, a UV absorber or a UV absorber mixture and, if appropriate, one or more additives selected from the group consisting of viscosity-regulating thickeners, fillers or solvents, which comprises 40 to 98% by weight of the UV absorber or of the UV absorber mixture, 0.01 to 30% by weight of one or more signal substance(s), and 0.1 to 20% by weight of one or more pesticidally active compound(s) selected from the group consisting of the compounds of the formula

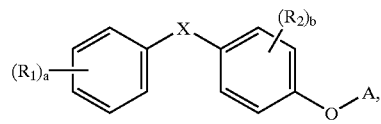

(I)

in which a is 0, 1 or 2, where, if a is 2, the two radicals $R_1$ are identical or different, b is 0, 1 or 2, where, if b is 2, the two radicals $R_2$ are identical or different;

X is methylene, O, S or C(=O), $R_1$ is $C_1$–$C_3$alkyl, halo-$C_1$–$C_3$alkyl, $C_1$–$C_3$alkoxy, halo-$C_1$–$C_3$alkoxy, fluorine, chlorine or bromine;

$R_2$ is halogen, nitro, $C_1$–$C_6$alkyl, phenyl-$C_1$–$C_6$alkyl, halo-$C_1$–$C_4$alkyl, $C_1$–$C_3$alkoxy, halo-$C_1$–$C_3$alkoxy, $C_2$–$C_4$alkenyl, $C_2$–$C_4$alkynyl, $C_1$–$C_3$alkoxyalkyl or $C_3$–$C_6$cycloalkyl, and A is $C_1$–$C_6$alkyl, $C_2$–$C_6$alkenyl or $C_3$–$C_6$alkynyl, which are unsubstituted or substituted by a substituent selected from the group consisting of $C_1$–$C_6$alkoxy, $C_2$–$C_6$alkenyloxy, $C_3$–$C_6$alkynyloxy, —O—N=$CH_2$, —O—N=CH—$C_1$–$C_6$alkyl, phenoxy, pyridyl, pyridyloxy, phenyl and phenyl, which is substituted by a substituent selected from the group consisting of $C_1$–$C_6$alkyl or —O—$CH_2$—O—; or A is a radical (Ib)

$$-(CH_2)_2-\underset{\underset{Y}{\|}}{\overset{R_7}{\underset{|}{N}}}-R_6, \quad\text{(Ib)}$$

where $R_6$ is $C_1$–$C_6$alkyl, phenyl-$C_1$–$C_6$alkyl, halo-$C_1$–$C_4$alkyl, $C_2$–$C_4$alkenyl, $C_2$–$C_4$alkynyl, $C_1$–$C_6$ alkoxy, phenoxy, phenyl-$C_1$–$C_6$alkoxy, halo-$C_1$–$C_4$alkoxy or $C_3$–$C_6$ cycloalkyl;

$R_7$ is hydrogen, $C_1$–$C_6$ alkyl, phenyl-$C_1$–$C_6$ alkyl, halo-$C_1$–$C_4$alkyl, $C_2$–$C_4$alkynyl, $C_1$–$C_3$alkoxyalkyl or $C_3$–$C_6$cycloalkyl; and Y is O or S; in free form or in salt form;

said composition having a viscosity of between 10,000 and 30,000 op; and being distributed as 100 to 1500 microdrops per 1000m$^2$ of the cultivated area to be protected; and wherein the males of said insects and representatives of the order Acarina are attracted by said composition and wherein the composition taken up by the males is transferred to the females thus connecting said eggs.

2. A method according to claim 1 wherein the composition is distributed on an agriculturally cultivated area.

3. A method according to claim 1 wherein the composition is distributed uniformly over the cultivated area to be protected in the form of microdrops in a range of from 5 to 3,000μl.

4. A method according to claim 3 wherein the microdrops are distributed to the plants to be protected.

* * * * *